(12) United States Patent
Bao et al.

(10) Patent No.: US 12,099,546 B2
(45) Date of Patent: Sep. 24, 2024

(54) CYCLIC MEMORY MANAGEMENT FOR WEB-BASED MEDICAL IMAGE VIEWERS

(71) Applicant: GE Precision Healthcare LLC, Milwaukee, WI (US)

(72) Inventors: Yongjian Bao, Vernon Hills, IL (US); Sayooj Cyriac, Arlington Heights, IL (US); Arjun Reddy Rachuri, Naperville, IL (US); Trivedi Kumar Bodlapati, Aurora, IL (US); Rahul Basavraj Ghiware, Naperville, IL (US)

(73) Assignee: GE Precision Healthcare LLC, Waukesha, WI (US)

( * ) Notice: Subject to any disclaimer, the term of this patent is extended or adjusted under 35 U.S.C. 154(b) by 364 days.

(21) Appl. No.: 17/566,176

(22) Filed: Dec. 30, 2021

(65) Prior Publication Data

US 2023/0214420 A1 Jul. 6, 2023

(51) Int. Cl.
| | | |
|---|---|---|
| G06F 16/54 | (2019.01) | |
| G06F 16/51 | (2019.01) | |
| G06F 16/957 | (2019.01) | |
| G16H 10/60 | (2018.01) | |
| G16H 30/20 | (2018.01) | |
| G16H 30/40 | (2018.01) | |

(52) U.S. Cl.
CPC .............. *G06F 16/54* (2019.01); *G06F 16/51* (2019.01); *G16H 30/20* (2018.01); *G06F 16/9574* (2019.01); *G16H 10/60* (2018.01); *G16H 30/40* (2018.01)

(58) Field of Classification Search
CPC ...... G06F 16/51; G06F 16/54; G06F 16/9574; G16H 10/60; G16H 30/20; G16H 30/40

USPC ......................................................... 382/305
See application file for complete search history.

(56) References Cited

U.S. PATENT DOCUMENTS

| | | | | |
|---|---|---|---|---|
| 6,243,095 B1* | 6/2001 | Shile | ...................... | A61B 6/463 715/854 |
| 8,682,142 B1* | 3/2014 | Boskovitz | ............ | G11B 27/034 386/282 |
| 2006/0114254 A1* | 6/2006 | Day | ........................ | G06T 15/08 345/424 |
| 2008/0021730 A1* | 1/2008 | Holla | ...................... | G16H 80/00 705/2 |

(Continued)

*Primary Examiner* — Kenny A Cese
(74) *Attorney, Agent, or Firm* — Amin, Turocy & Watson, LLP

(57) ABSTRACT

A system comprises a memory that stores computer executable components; and a processor that executes the computer executable components stored in the memory. A communication component receives a stream of medical images from a medical image data source via a network for displaying in one or more viewports of a medical image visualization application that provides interactive functionalities in association with the displaying. A buffer component stores the medical images, in one or more buffers, as the respective medical images are received. A monitoring component monitors user activity with respect to a rendered subset of the medical images in the one or more viewports in association with usage of the interactive functionalities. A buffer management component regulates storing of the medical images in the one or more buffers by the buffer component as a function of the user activity to facilitate seamless rendering of the medical images.

20 Claims, 9 Drawing Sheets

(56) References Cited

U.S. PATENT DOCUMENTS

| | | | | |
|---|---|---|---|---|
| 2014/0153358 | A1* | 6/2014 | Balakrishnan | A61B 8/463 367/7 |
| 2020/0310611 | A1* | 10/2020 | Vincent | G09G 5/393 |
| 2022/0279602 | A1* | 9/2022 | Xue | H04W 52/0241 |

* cited by examiner

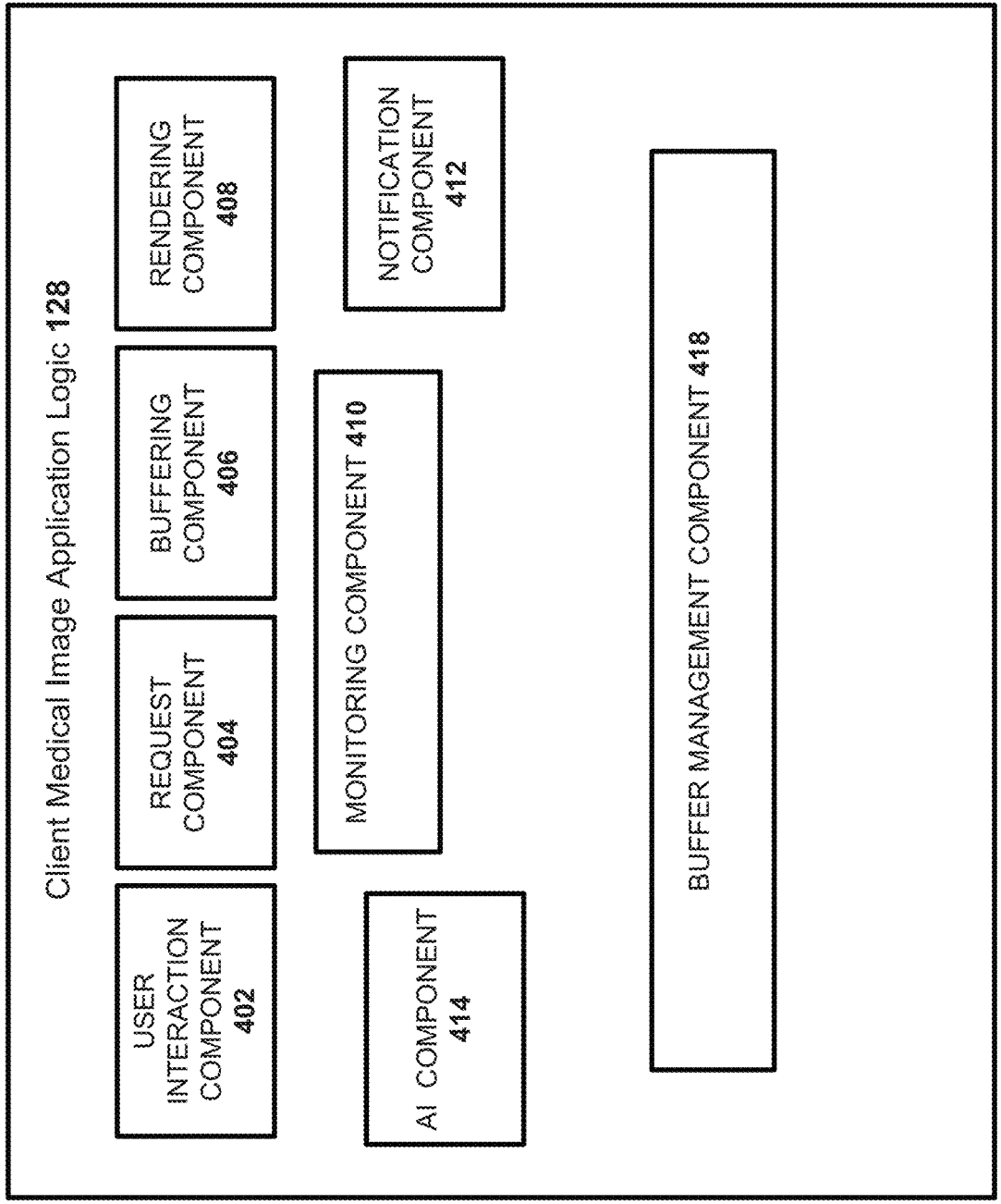

CYCLIC MEMORY MANAGEMENT FOR WEB-BASED MEDICAL IMAGE VIEWERS

TECHNICAL FIELD

This application relates to web-based medical imaging viewers and more particularly to cyclic memory management techniques that facilitate seamless rendering of medical images via a web-based medical imaging viewer.

BACKGROUND

Advancements in internet technologies such as Hyper Text Markup Language 5 (HTML5) have enabled creation of advanced and rich web-based medical image view applications that allow radiologists to easily access teleradiology systems and remotely view medical images. Compared with picture archiving and communication systems or other imaging workstations which require dedicated hardware and software, a web-based application can be run on almost all personal computers without the need for powerful equipment on the client side. For example, cloud computing has been used in the field of medical imaging for high-capacity storage, sharing, and intensive computational tasks. In this infrastructure, image data and complex processing tasks are moved from user computers to the cloud. Users then launch a browser to access the cloud that allows visualization of medical image directly via HTML. In this case, a radiologist can implement the cloud-based medical image analysis using a personal computer from any location.

However, successful implementation of a cloud-based teleradiology system requires a fast network and easy access. In this regard, remote viewing of radiological images is heavily dependent on network capabilities. When internet connections are slow or unavailable, the web-based medical image viewer cannot receive and display medical images in seamless manner on demand. In addition, level of support and expected performance of the viewer application can vary depending on capabilities of a client browser. In this regard, memory capacity of the browser is typically limited to a very small portion of the entire local memory of the client device (e.g., typically 1-2 Gigabytes (GB)). Accordingly, techniques for managing browser memory constraints in association with providing seamless rendering of streamed medical image content via a web-based application are needed.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments, systems, computer-implemented methods, apparatus and/or computer program products are described that facilitate seamless rendering of medical images via a web-based medical imaging viewer using cyclic memory management techniques.

According to an embodiment, a system, comprises: a memory that stores computer executable components; and a processor that executes the computer executable components stored in the memory, wherein the computer executable components comprise: a communication component that receives a stream of medical images from a medical image data source via a network for displaying in one or more viewports of a medical image visualization application that provides interactive functionalities in association with the displaying; a buffer component that stores the medical images, in one or more buffers, as the respective medical images are received; a monitoring component that monitors user activity with respect to a rendered subset of the medical images in the one or more viewports in association with usage of the interactive functionalities; and a buffer management component that regulates storing of the medical images in the one or more buffers by the buffer component as a function of the user activity to facilitate seamless rendering of the medical images.

In an aspect, the system further comprises a rendering component that regulates speed of rendering of a subset of the medical images as a function of amount of the subset of medical images data respectively buffered.

In another embodiment, each of the one or more viewports has a dedicated buffer.

In yet another embodiment, speed of buffering in respective dedicated buffers is a function of user activity within respective viewports.

In still another aspect, the speed of buffering in the respective dedicated buffers is a function of network bandwidth.

In an aspect, the system further comprises an artificial intelligence (AI) component that facilitates regulating the speed of buffering in the respective dedicated buffers as a function of inferred future user activity within the respective viewports.

In another aspect, the AI component facilitates regulating rendering of respective medical images as a function of the inferred future user activity within the respective viewports.

In yet another aspect the system further comprises a rendering component that renders a subset of the medical images in respective viewports, and regulates the rendering of the subset of the medical images as a function of medical image data buffered in the respective dedicated buffers.

In still another aspect, the rendering component skips rendering of frames of the respective medical image data to maintain frame per second rendering of the respective medical image data.

In an aspect, the system further comprises a notification component that alerts a viewer when frames of the respective medical image data are skipped.

In yet another aspect, the system further comprises a weighting component that weights requests for the respective medical image data as a function of priority of display criteria per viewport.

In an embodiment, a computer-implemented method employs a processor and memory to implement acts, comprising receiving, using a communication component, a stream of medical images from a medical image data source via a network for displaying in one or more viewports of a medical image visualization application that provides interactive functionalities in association with the displaying; storing, using a buffer component, the medical images in one or more buffers as the respective medical images are received; monitoring, using a monitoring component, user activity with respect to a rendered subset of the medical images in the one or more viewports in association with usage of the interactive functionalities; and regulating, using a buffer management component, storing of the medical images in the one or more buffers by the buffer component as a function of the user activity to facilitate seamless rendering of the medical images.

In an aspect, the method further comprises regulating, using a rendering component, speed of rendering of a subset of the medical images as a function amount of the subset of medical images data respectively buffered.

In another embodiment, a non-transitory machine-readable storage medium, comprises executable instructions that, when executed by a processor, facilitate performance of operations, comprising: receiving a stream of medical images from a medical image data source via a network for displaying in one or more viewports of a medical image visualization application that provides interactive functionalities in association with the displaying; storing the medical images in one or more buffers as the respective medical images are received; monitoring user activity with respect to a rendered subset of the medical images in the one or more viewports in association with usage of the interactive functionalities; and regulating storing of the medical images in the one or more buffers by the buffer component as a function of the user activity to facilitate seamless rendering of the medical images. In some embodiments, elements described in connection with the disclosed systems can be embodied in different forms such as a computer-implemented method, a computer program product, or another form.

DESCRIPTION OF THE DRAWINGS

FIG. 4 illustrates example client medical image application logic components in accordance with one or more embodiments of the disclosed subject matter.

DETAILED DESCRIPTION

Figure 1:
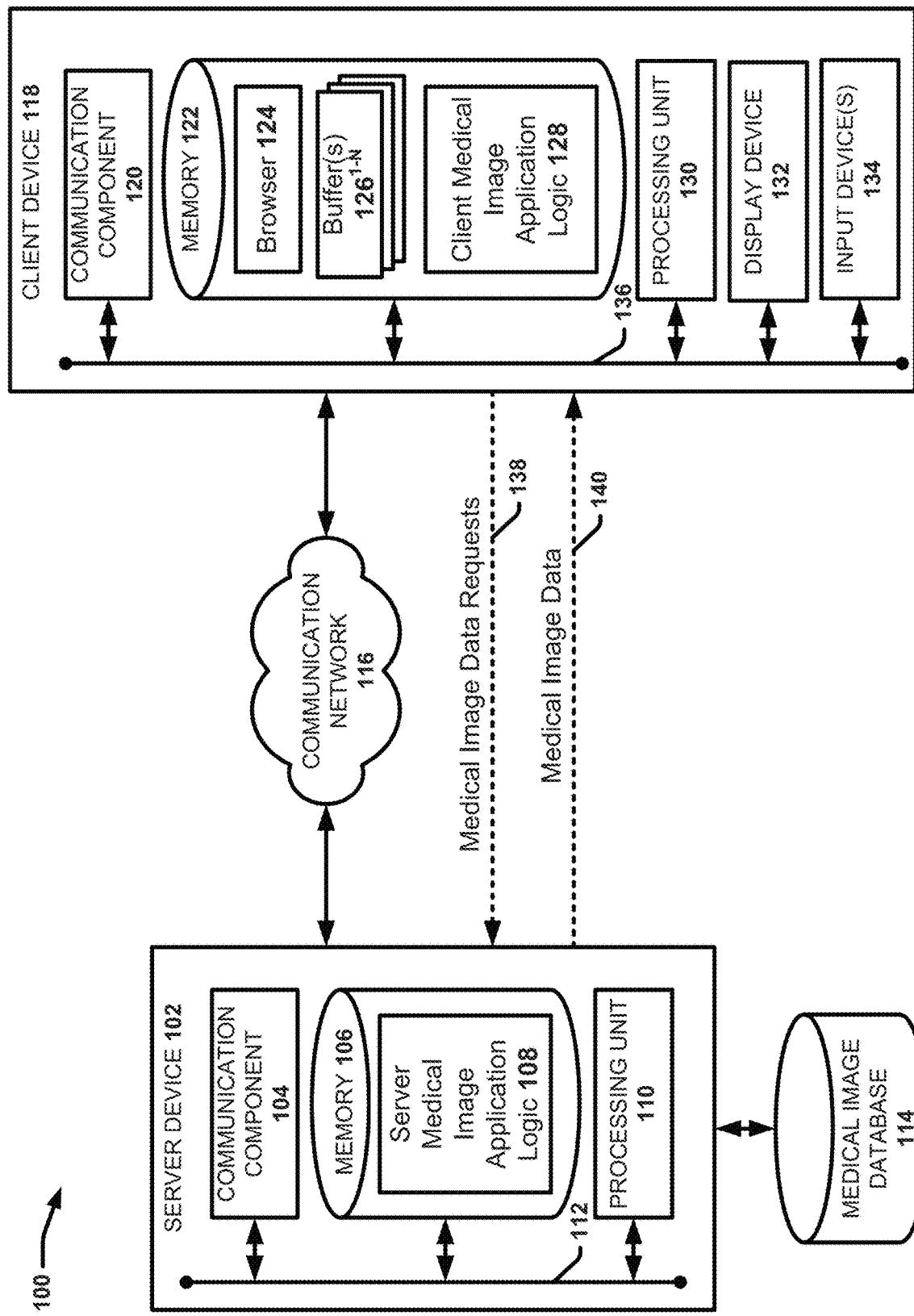
FIG. 1 illustrates a block diagram of an example, non-limiting system that facilitates seamless rendering of medical images via a web-based medical imaging viewer using cyclic memory management techniques in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Background section, Summary section or in the Detailed Description section.

The disclosed subject matter is directed to systems, computer-implemented methods, apparatus and/or computer program products that facilitate seamless rendering of medical images via a web-based medical imaging viewer application in association with accounting for network bandwidth latency fluctuations. In one or more embodiments, the disclosed subject matter provides a web-based medical image viewer application that provides for accessing and viewing medical images at a client device using a web-browser deployed at the client device. The application can provide various interactive functions associated with accessing and viewing the medical images using a web-browser, including selecting specific images or imaging studies for viewing in one or more viewports of a graphical user interface of the web-application, navigating or scrolling through respective medical images included in a series, manipulating the images (e.g., zooming, editing, annotating, etc.), and so one. For example, in various embodiments, the application can provide for downloading medical images included in a stack or series selected for viewing, storing the downloaded images in browser buffer, displaying individual images included in the series in a dedicated viewport in cine mode, and scrolling through the respective images within the viewport as function of received user navigational input commands. As applied to medical images, cine mode refers to automatically displaying respective medical images included in a sequence in a movie mode, wherein each image frame is automatically displayed frame by frame at a controlled frame per second (FPS) rate. The application can further support various user interface display formats or layouts, including a plurality (e.g., two or more) dedicated viewports adapted to display different subsets of images, such as different series or stacks of images associated with the same patient or different patients.

The application further incorporates a cyclic memory management design for the buffer memory that facilitates seamless rendering in association with displaying a sequence of medical images within a viewport. In various embodiments, the application can employ a separate dedicated buffer for each viewport, wherein the medical image data in each buffer is managed in accordance with user interactions on the respective viewport, network bandwidth latency fluctuations, and the fixed memory capacity of each buffer. In this regard, each buffer is a circular queue that loads received medical images requested for viewing in the corresponding viewport into the buffer memory as they are downloaded from the application server. The cyclic buffer has a limited or fixed size/memory capacity and the cyclic memory management design provides for overwriting previously stored content in the buffer once capacity has been reached to maintain a subset of the images associated with the set (e.g., series/stack etc.) of images selected for viewing in the corresponding viewport, wherein the current subset of images stored in the viewport is adapted to include those images most relevant to the current rendering context. For example, assuming the user has selected a particular medical image series for viewing in a viewport sequentially frame-by-frame and the entire image series memory requirements exceeds the corresponding dedicated buffer capacity. In this case, the cyclic memory management scheme can overwrite previously stored images in the series based on the relative position of the currently displayed image in the series to remove images that have a series position that is far from the position of the currently displayed image and thus are unlikely to be called for viewing from the buffer, assuming the user is viewing the images sequentially (e.g., either scrolling forward, scrolling backward, or in cine mode). In this regard, the cyclic memory management scheme strives to always maintain a subset of the entire image series for each viewport and maximizes the user experience with this subset (or a window from the entire set). Combined with smart download, the buffer is intended to optimize the rendering experience in the viewport from the perspective of the viewer by providing seamless rendering of all the images in the series in a cyclic manner.

The application further regulates the rate at which the images are downloaded and stored in each viewport dedicated buffer memory relative to the rate at which the images are rendered in the viewport as function of manual scrolling or automatic scrolling in cine mode. The application also regulates the rendering speed based on the download rate, the current position of a rendered images in a sequence of images selected for viewing in the corresponding viewport, and the amount of buffered image content currently available in the buffer in order to prevent rendering interruptions/delays. To facilitate this end, the application decouples the image downloading and display processes. Each viewport dedicated buffer can be adapted to download and store respective images included in a series from the server frame by frame in an order defined by the series and maintain a buffered amount of images in the series in the buffer. The application further monitors the relative position of the most recently downloaded frame in the buffer, (referred to herein as the Head (H) position), relative to the position of the currently displayed frame, (referred to herein as the Tail (T) position), and adapts the rendering process and/or the downloading process to maintain T behind H and to ensure the rate at which T approaches H achieves a desired frame per second (FPS) rendering speed. As a result, the application provides for adaptive data consumption based on changes in network bandwidth fluctuations.

For example, as the user is scrolling through sequential frames of an image study in a dedicated viewport frame by frame (e.g., image by image), the T and H position traverse in the same direction (e.g., right—scroll forward, left—scroll backward). Smooth image rending is achieved when the H and T traverse in a uniform pace, especially in the case for cine viewing to achieve a consistent FPS rate. Network bandwidth latency fluctuations can be detected by monitoring the H position. In this regard, if H moves slower than T, this implies that the image download rate has slowed down relative to current rendering rate demanded by the viewport (e.g., based on the user scrolling speed and/or a pre-set FPS speed for an activated cine viewing mode). In this scenario, the system 100 may take action by slowing down the rendering rate to a slower FPS. Additionally, or alternatively, the application can adjust the download process by skipping downloading of a subset of frames (e.g., medical images) included in the series. For instance, the application may skip downloading every other frame in the series, thereby increasing the download rate by 100%. As medical images in a series typically reflect a slightly different scan image relative to the preceding and subsequent frames, from the perspective of the viewer, the images sequentially during operation in this skipping mode will still provide a sequential view of the captured anatomical region. Similarly, image rendering performance can be detected by monitoring the T position. For example, if T traverses slower than H, this implies image rendering maybe slower than the download rate. In this scenario, the application can adjust the download process associated with that viewport by assigning higher priority to image data requests associated other viewports whose demand for downloaded image content is higher (e.g., based on active rendering rate demanded by that viewport). The system 100 can also take action by skipping frames during rendering to maintain a desired FPS rendering rate.

The disclosed techniques for incorporate priority-based image download service requests per viewport. In this regard, each viewport dedicated buffer can request medical image content from the server in accordance with a priority weighting scheme. The priority weighting scheme can assign a weight to image data requests for frames coming from each viewport, wherein requests associated with viewports having a higher demand for image content are served before request associated with viewports having a lower demand for image content. For example, image data requests associated with a viewport that is actively rendering medical images in cine mode can be processed before image data requests from an inactive viewport in which the user is not actively scrolling.

Various embodiments of the disclosed subject matter are directed to facilitating smooth rending of medical images in the context of viewing a sequence of medical images in cine mode or a manual scrolling mode, wherein individual images in the sequence are displayed in a single viewport one at time in a frame-by-frame manner. With these embodiments, the sequence of medical images can correspond to a series or stack of medical images that were captured and/or generated according to a defined sequential order. For example, the sequence of medical images may include respective medical images captured in series in association with a three-dimensional medical (3D) imaging scan, such as a computed tomography (CT) scan, a magnetic resonance imaging (MRI) scan), or the like. With these technologies, each medical image in the series corresponds to a different image frame captured of an anatomical region of interest from a slightly different perspective relative to the previously captured image. However, the disclosed techniques can be applied to rendering a variety of different medical images sets, wherein the respective images in the set are arranged according to a defined order or sequence and is not limited to medical image series or 3D medical imaging modalities. In this regard, the types of medical images that can be streamed and rendered using the disclosed web-based medical image viewer application and corresponding systems can include images captured using various types of image capture modalities. For example, the medical images can include (but are not limited to): radiation therapy (RT) images, X-ray (XR) images, digital radiography (DX) X-ray images, X-ray angiography (XA) images, panoramic X-ray (PX) images, computerized tomography (CT) images, mammography (MG) images (including a tomosynthesis device), a magnetic resonance imaging (MR) images, ultrasound (US) images, color flow doppler (CD) images, position emission tomography (PET) images, single-photon emissions computed tomography (SPECT) images, nuclear medicine (NM) images, MRI images, and the like. The medical images can also include synthetic versions of native medical images such as synthetic X-ray (SXR) images, modified or enhanced versions of native medical images, augmented versions of native medical images, and the like generated using one or more image processing techniques. The terms medical image, image frame, frame, scan, scan slice and the like are used herein interchangeably to refer to a single medical image.

The term "web platform" as used herein refers to any platform that enables delivery of content and services over a network (i.e., the web/Internet) using a network transfer protocol, such as hypertext transfer protocol (HTTP), HTML5, sFTP, or another network transfer protocol. For example, a web platform can include, but is not limited to, a web-application (i.e., an interactive website), a mobile website, a mobile application or the like. The terms "web platform," "web-based platform," "network platform," "platform," and the like are used herein. interchangeably unless context warrants particular distinction amongst the terms.

The terms "algorithm" and "model" are used herein interchangeably unless context warrants particular distinction amongst the terms. The terms "artificial intelligence (AI) model" and "machine learning (ML) model" are used herein interchangeably unless context warrants particular distinction amongst the terms.

The term "application" as employed herein is intended to convey the functionalities provided by system 100.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

FIG. 1 illustrates a block diagram of an example, non-limiting system 100 (also referred to as system 100) that facilitates seamless rendering of medical images via a web-based medical imaging viewer (e.g., visualization application, image viewer, viewer application) in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

System 100 includes a server device 102 that is employed to stream medical image data to a client device 118 in association with usage of a web-based medical image visualization application. The server device 102 includes a communication component 104 for communicating with the client device 118 (via communication component 120) via a communication network 116. The server 102 includes a memory 106 and a processing unit 110. A distributed application (that includes server medical image application logic 108 and client medical image application logic 128) facilitates generating visualizations of the medical image data at the client device 118. In an embodiment, the distributed application can be web-based (e.g., utilizing a browser 124). The medical image data can reside in a medical image database 114, which can for example reside at the server, across multiple storage devices, in a distributed framework, etc. The client device 118 can make medical image data requests 138 to the server 102, and in response to such requests 138, transmit or stream medical image data 140 to the client device 118. The client device 118 likewise includes a memory 122, a processing unit 130, a browser 124, buffers 126, display device 132 and input devices 134.

As used herein, the machine can be and/or can include one or more of a computing device, a general-purpose computer, a special-purpose computer, a quantum computing device (e.g., a quantum computer), a tablet computing device, a handheld device, a server class computing machine and/or database, a laptop computer, a notebook computer, a desktop computer, a cell phone, a smart phone, a consumer appliance and/or instrumentation, an industrial and/or commercial device, a digital assistant, a multimedia Internet-enabled phone and/or another type of device. Examples of said and memory 106 and processing unit 110 as well as other suitable computer or computing-based elements, can be found with reference to FIG. 8 (e.g., with reference to processing unit 804 and system memory 806), and can be used in connection with implementing one or more of the systems or components shown and described in connection with FIG. 1 or other figures disclosed herein.

The deployment architecture of system 100 can vary. In embodiments, one or more of the components of system 100 can be deployed in a cloud architecture, a virtualized enterprise architecture, or an enterprise architecture wherein one the front-end components and the back-end components are distributed in a client/server relationship. With these embodiments, the features and functionalities of one or more components described herein, can be deployed as a web-application, a cloud-application, a thin client application, a thick client application, a native client application, a hybrid client application, or the like. Various example deployment architectures for system 100 (and other systems described herein) are described infra with reference to FIGS. 8-9.

Turning back to FIG. 1, in an aspect, a stream of medical images 140 is received (e.g., using communications component 120) from server device 102 accessing medical image database 114 via network 116 for displaying in one or more viewports of a medical image visualization application (utilizing application logic 108 and 128) that provides interactive functionalities in association with displaying the medical image data 140 at the client device 118. In other words, a user (e.g., medical worker) viewing medical image data in a visualization application at the client device 118. As discussed, the server 102 streams the medical image data 140 to client device 118 employed by the user, and the medical image data 140 is rendered via the visualization application. The visualization application can utilize one or more viewports (See FIG. 2 and associated discussion). A viewport can be akin to a viewing window, portal, display or the like. Oftentimes, medical workers multi-task or multi-view by viewing multiple images across one or more displays.

The streamed medical images 140 from the server 102 are stored in one or more buffers 126 as the respective medical images (or medical image data 140) are received. The received medical image data 140 is respectively buffered to facilitate seamless rendering of respective medical images. For example, if network bandwidth across network 116 is insufficient, the streamed medical image data 140 can result in choppy rendering. By buffering such medical image data, rendering of the medical image data can be presented in a seamless and smooth manner. However, medical image data can often be voluminous, and network and hardware resources limited. Consequently, conventional medical image rendering systems often fall short due to inefficient resource allocation and data management. The subject innovation facilitates real-time assessment of data needs at a viewport and user activity and inferred future activity level to optimize resource allocation (e.g., buffering, streaming priority, weighting, etc.) to facilitate seamless rendering of medical image data as needed based on limited resources.

In an aspect, user activity can be monitored (e.g., using a monitoring component 410 (see FIG. 4 and discussion)) with respect to a rendered subset of the medical images in the one or more viewports in association with usage of the interactive functionalities. By monitoring user activity, data needs with respect to streaming, prioritizing streaming, data requests, buffering, etc., can be determined or inferred in order to facilitate provisioning and rendering of medical image data per determined or inferred user needs. In an embodiment, an AI component 430 (FIG. 4) can facilitate making such determinations or inferences using models (trained explicitly or implicitly) that leverage historical usage cases, user preferences, known tasks, data types, etc. Accordingly, based on context of a user, task(s), resources, etc. data requests, data buffering, data rendering, can be regulated to optimize a visualization experience given a set of resources and associated constraints or limitations. Regulation of storing of the medical images in the one or more buffers by a buffer component 406 (FIG. 4) is performed as a function of the user activity to facilitate seamless rendering of the medical images.

In another aspect, medical image data requests 138 can be weighted to facilitate seamless rendering of the respective medical image data 140 across respective viewports as a function of display criteria per viewport and available resources (e.g., buffer capacity, processing capacity, network bandwidth, current user activity, inferred future user activity, etc.). Further discussion regarding such embodiment is presented infra in connection with FIG. 5 and associated description.

Figure 2:
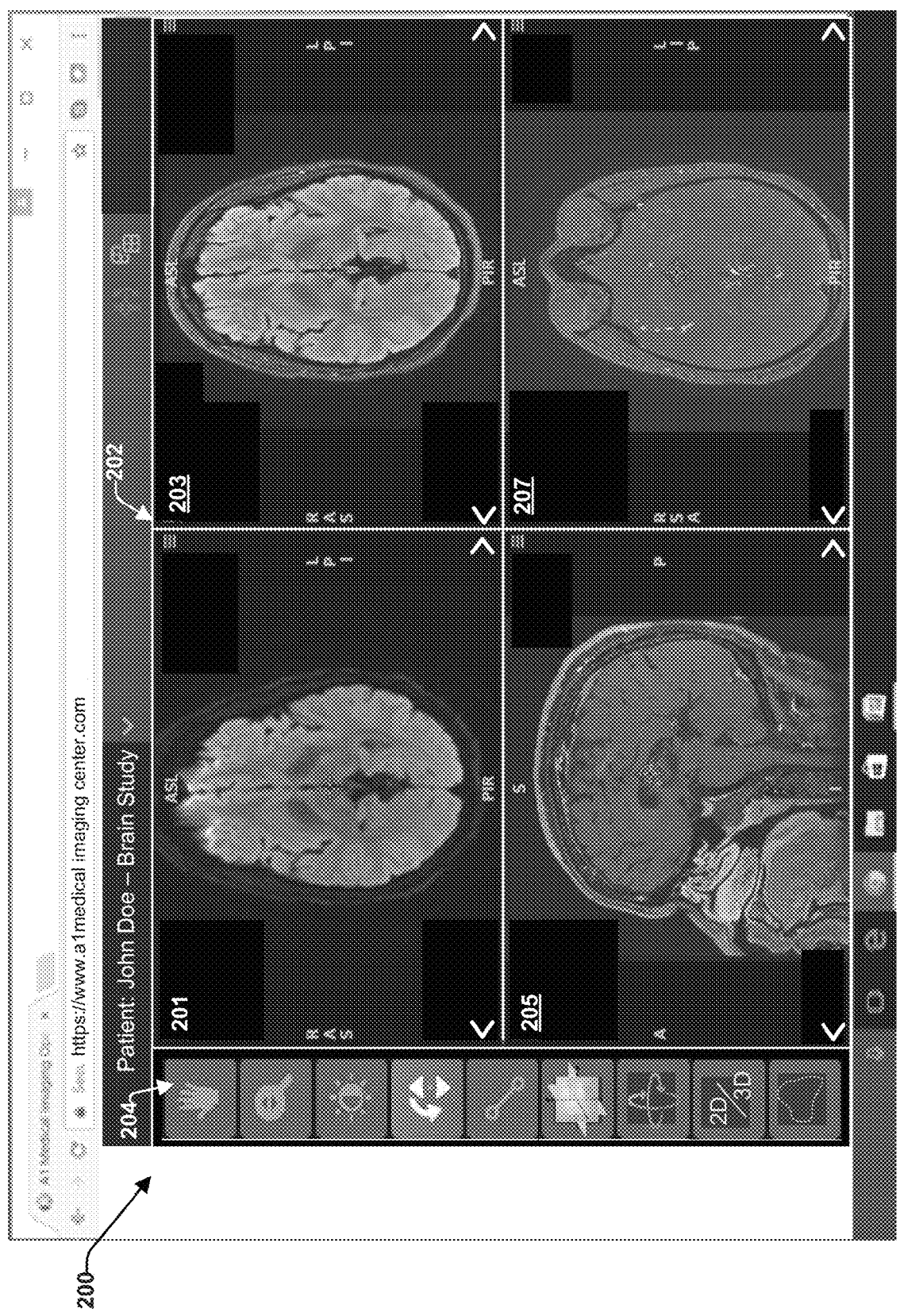
FIG. 2 presents an example graphical user interface of a web-based medical imaging viewer in accordance with one or more embodiments of the disclosed subject matter.

FIG. 2 presents an example graphical user interface (GUI) 200 employed by a web-based medical imaging application in accordance with one or more embodiments of the disclosed subject matter. The example GUI 200 corresponds to one visualization that can be displayed at the client device 118 (via the display device 134) in association with usage of the web-based medical imaging application (provided by the server medical image application logic 108 and/or the client medical image application logic 128). In the embodiment shown, the GUI 200 is rendered using a browser 124 within a display window of a webpage. However, it should be appreciated that the disclosed subject matter is not limited to this rendering format.

As illustrated, the GUI 200 includes a primary display area 202 that can include a plurality of different viewports, respectively identified as viewport 201, viewport 203, viewport 205 and viewport 207. Although four viewports are shown, it should be appreciated that the number of viewports provided by the imaging application can vary and include one or more viewports. Each viewport can be adapted to display a different set of medical images, such as a different medical image series or stack. For example, in in the embodiment shown, each viewport represents a different set of related brain scan MRI images corresponding to a different DICOM series for patient John Doe series. Each viewport can be adapted to display a single medical image included in each set one at a time and provides for scrolling through the respective medical images in the set in a frame-by-frame manner. For example, in the embodiment shown, each viewport includes forward and backward scrolling widgets (e.g., represented by the forward and back arrows located in the lower right and left corners of each viewport) that can be selected to manually scroll through the respective images in the corresponding viewport in sequential order in the forward and reverse directions. Additionally, or alternatively, the application can support a cine viewing mode within each viewport, wherein upon selection activation of the cine viewing mode, the application begins rendering the respective images included in each within its corresponding viewport sequentially wherein the rendering frame per second (FPS) rate is automatically controlled to move to the next sequential image in the set as if viewing the images as a movie. In some implementations, the GUI 200 can include one or more control icons 204 that provide for initiating a viewing session, selecting an imaging study or medical image data set for viewing, closing the viewing session, returning to a previous screen, and the like that can provide various functionalities for interacting and viewing the rendered image content.

In various embodiments, upon initiation of the application, the user can provide input selecting or indicating the particular medical image study for viewing within each viewport. Based on this received input, the application (as implemented by system 100) can initiate downloading of corresponding images included in each set from the server device 102 (e.g., using the communication component 120 and the browser 124). The order in which the application downloads the respective images included in each set can be based on the defined order of the respective images in the set. For example, assuming a set of images comprising sequentially ordered frames, the application can be configured to download the frames sequentially starting with the first ordered image in the set, followed by the second, then the third and so on. As discussed in greater detail infra, in some implementations, the application can activate a frame skipping mode in which some frames as skipped for downloading to account for system bandwidth latency constraints (e.g., every other, every third frame, every four frame, and/or select frames considered less relevant to the viewing context as determined based on predefined criteria and/or inferred user relevance).

With reference to FIGS. 1 and 2, as described with reference to FIG. 1, each viewport (e.g., of the viewports 201, 203, 205 and 207) can include a dedicated buffer 126 (of buffers $126^{1-N}$) in which the downloaded images in each set for each corresponding viewport are stored. Once at least one image in each set has been downloaded and stored in its corresponding buffer, the application can begin rendering the buffered images within the corresponding viewport. In various embodiments, the application can by default display the first image in each series within the corresponding viewport. As more images associated with each viewport image set are downloaded and added to the buffer, the application can allow for scrolling through the respective images and/or viewing the respective images in cine mode.

The system 100 further incorporates a cyclic memory management design for each dedicated buffer $126^{1-N}$ that facilitates seamless rendering in association with displaying sequence of medical images within a viewport while accounting for network bandwidth latency fluctuations, user interactions within each viewport, the fixed memory capacity of each buffer, and image data content priority weights associated with each viewport.

FIGS. 3A-3D schematically illustrate usage of a cyclic memory buffer (e.g., buffer $126^1$) for storing medical images in association with a web-based medical imaging viewer in accordance with one or more embodiments of the disclosed subject matter. As illustrated in FIGS. 3A-3D, each buffer $126^{1-N}$ can employ a cyclic architecture for storing medical images downloaded from the server device 102. In this regard, FIGS. 3A-3D illustrate the progression of one example buffer $126^1$ that can correspond to the dedicated buffer for one viewport. Each buffer is a circular queue that loads received medical images requested for viewing in the corresponding viewport into the buffer memory as they are downloaded from the application server. The system 100 further regulates the rate at which the images are downloaded and stored in each viewport dedicated buffer memory relative to the rate at which the images are rendered in the viewport as function of manual scrolling or automatic scrolling in cine mode. To facilitate this end, the system 100 decouples the image downloading and display/rendering processes. Each viewport dedicated buffer can be adapted to download and store respective images included in a series from the server frame by frame in an order defined by the series and maintain a buffered amount of images in the series in the buffer.

Figure 3A:
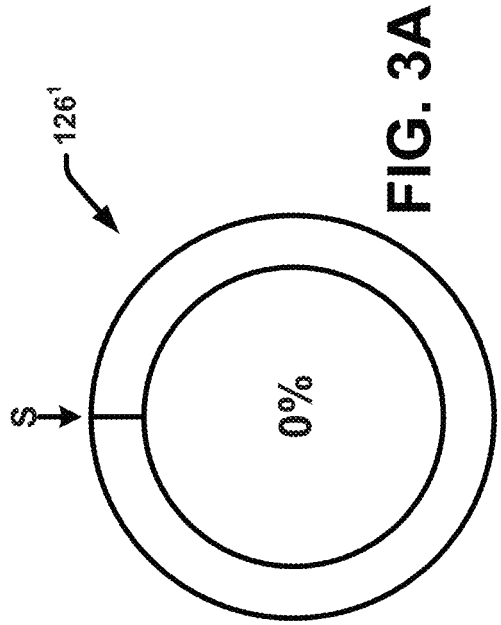
FIGS. 3A-3D illustrate usage of a cyclic buffer for storing medical images in association with a web-based medical imaging viewer in accordance with one or more embodiments of the disclosed subject matter.
Figure 3B:
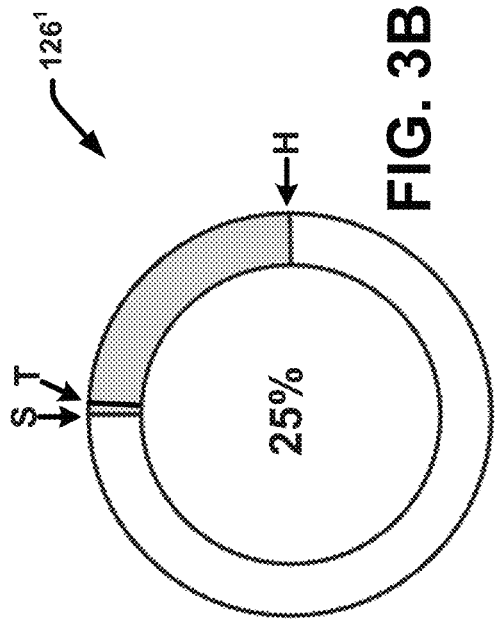
Figure 3C:
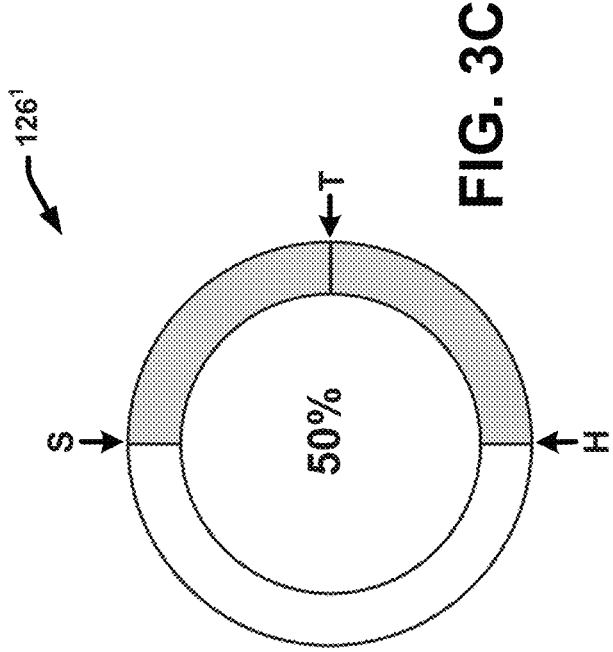
Figure 3D:
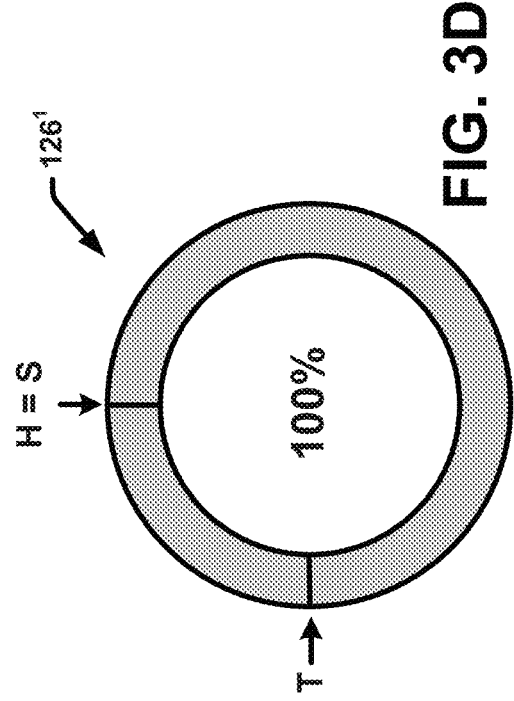

For example, FIG. 3A illustrates the buffer 126$^1$ at empty prior to downloading of medical image content. FIG. 3B illustrates the buffer 126$^1$ at 25% full. FIG. 3C illustrates the buffer 126$^1$ at 50% capacity, and FIG. 3D illustrates the buffer 126$^1$ at 100% full. In the respective FIGS. 3A-3D, S position indicates start position of writing to the buffer. The T position corresponds to position of currently displayed frame in a respective viewport, and the H position corresponds to the most recently downloaded frame in the buffer 126$^1$. The system 100 further monitors the relative position of the most recently downloaded frame in the buffer, (referred to herein as the Head (H) position), relative to the position of the currently displayed frame, (referred to herein as the Tail (T) position), and adapts the rendering process and/or the downloading process to maintain T behind H and to ensure the rate at which T approaches H achieves a desired frame per second (FPS) rendering speed. As a result, the system 100 provides for adaptive data consumption based on changes in network bandwidth fluctuations.

For example, as the user is scrolling through sequential frames of an image study in a dedicated viewport frame by frame (e.g., image by image), the T and H position traverse in the same direction (e.g., right—scroll forward, left—scroll backward). Smooth image rending is achieved when the H and T traverse in a uniform pace, especially in the case for cine viewing to achieve a consistent FPS rate. Network bandwidth latency fluctuations can be detected by monitoring the H position. In this regard, if H moves slower than T, this implies that the image download rate has slowed down relative to current rendering rate demanded by the viewport (e.g., based on the user scrolling speed and/or a pre-set FPS speed for an activated cine viewing mode). In this scenario, the system 100 may take action by slowing down the rendering rate to a slower FPS. Additionally, or alternatively, the application can adjust the download process by skipping downloading of a subset of frames (e.g., medical images) included in the series. For instance, the system 100 may skip downloading every other frame in the series, thereby increasing the download rate by 100%. As medical images in a series typically reflect a slightly different scan image relative to the preceding and subsequent frames, from the perspective of the viewer, the images sequentially during operation in this skipping mode will still provide a sequential view of the captured anatomical region. Similarly, image rendering performance can be detected by monitoring the T position. For example, if T traverses slower than H, this implies image rendering maybe slower than the download rate. In this scenario, the system 100 can adjust the download process associated with that viewport by assigning higher priority to image data requests associated other viewports whose demand for downloaded image content is higher (e.g., based on active rendering rate demanded by that viewport). The system 100 can also take action by skipping frames during rendering to maintain a desired FPS rendering rate. The system 100 strives to maintain H ahead of T so that sufficient image is stored for seamless rendering. Once the buffer 126$^1$ has reached full capacity as shown in FIG. 3D, the system 100 can selectively overwrite lower priority or lower relevance data (e.g., redundant data, data far from currently displayed image at position T).

FIG. 4 schematically illustrates an embodiment relating to the client medical image application logic 128. As noted a visualization application that renders medical images at client device 118 leverages application logic 108 at the server 102 and application logic 128 at the client device 118. The client logic 128 includes various components including user interaction component 402 that receives, interprets and executes user initiated commands corresponding to user intent. Request component 404 requests medical image data from the server 102. Buffering component 406 buffers (e.g., stores) the received medical image data in corresponding buffers 126 per viewport. Rendering component 408 renders subsets of the buffered image data. Monitoring component 410 monitors various events within the system 100, such as for example, user activity (e.g., scrolling, gazing, selecting, zooming, and other activities associated with visualizing and working with the medical image data. The monitoring component 410 can monitor download rate and buffer head position associated with respective buffers (e.g., rate at which H progresses relative to respective buffer capacity). The monitoring component 410 can monitor rendering rate of subsets of medical image data (e.g., rate at which T progresses relative to respective buffers).

A buffer management component 418 can regulate the medical image buffering across respective buffers as a function of viewport display criteria as discussed herein. It can prioritize frames, skip frames, overwrite data, etc. to regulate buffering rate as well as buffer capacity. The buffer management component 418 coordinate with the rendering component to optimize the visualization through coordinated buffering and rendering of image data. For example, the buffer management component 418 can instruct the rendering component to increase or decrease rate at which consecutive frames are rendered. A notification component 412 can notify a user when frames are skipped or rendering is altered, or other events related to the visualization. The server logic 128 can utilize artificial intelligence (AI) component 414 and/or associated models to facilitate servicing of the requests.

Given that the visualization application is a distributed application that resides at both server and client, it is to be appreciated that one or more functions performed at the server can in various embodiments be implemented at the client side and vice versa.

Conventional medical image rendering systems are often ineffective at rapidly rendering high-quality medical images due to voluminous size of medical images and limited hardware and network resources. Embodiments described and claimed herein overcome many deficiencies associated with conventional systems through dynamic weighting of data requests, strategic buffering of data across respective dedicated viewport buffers, factoring monitored user activity, learning historical user and task use scenarios, leveraging artificial intelligence and trained model(s) (explicitly and implicitly) to provide for a highly dynamic visualization system 100 that optimizes requesting, streaming, buffering and rendering of medical image data in a dynamic and adaptive manner to facilitate provisioning of a highly efficient visualization work environment, given available hardware and network resources, for a medical professional or the like.

Figure 5:
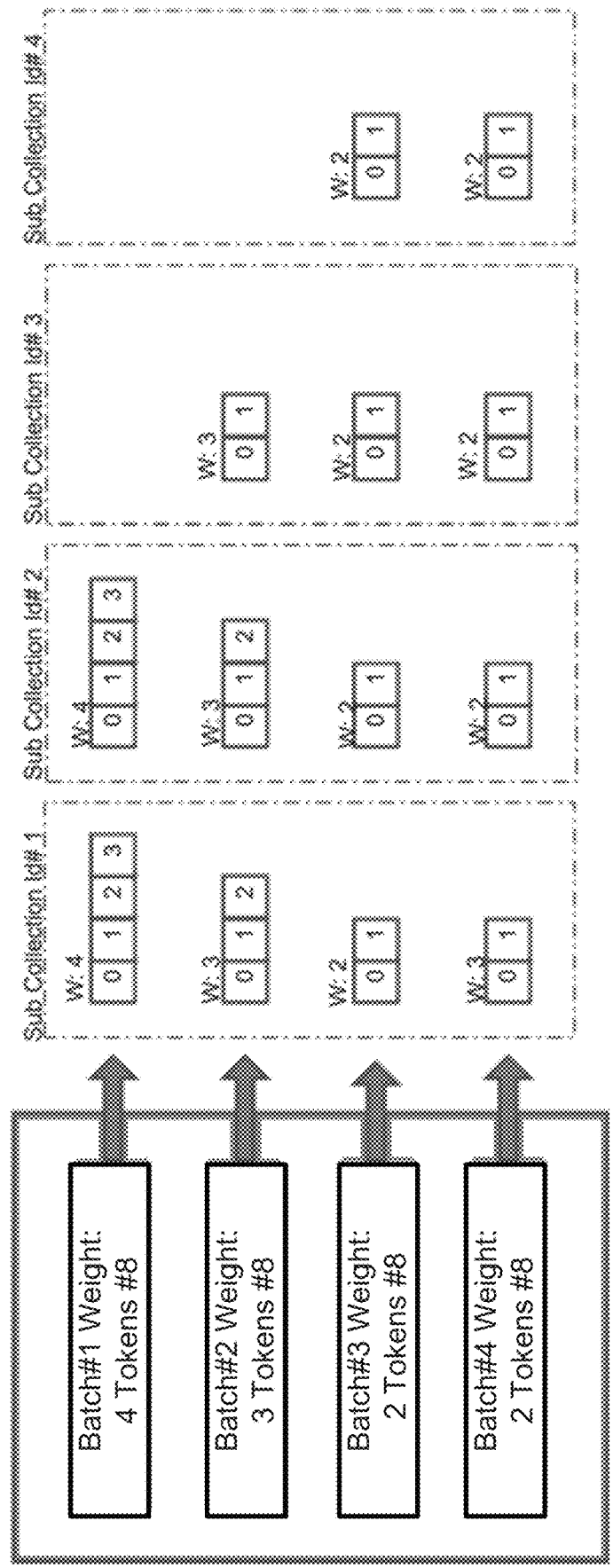
FIG. 5 illustrates priority based medical image data streaming request processing in accordance with one or more embodiments of the disclosed subject matter.

FIG. 5 schematically illustrates an embodiment relating to weighting medical image data requests to facilitate seamless rendering of respective medical image data across respective viewports as a function of display criteria per viewport and available resources (e.g., buffer capacity, processing capacity, network bandwidth, current user activity, inferred future user activity, etc.). In the diagram, a server is streaming medical image data to respective containers (e.g., associated with respective viewports) that are designated Sub-collection ID #1 . . . ID #4. As noted each viewport can have a dedicated buffer, and data requests are made to the server per image container or viewport. Since respective viewports can have different rendering needs, e.g., as a function of user activity or needs, data requests to the server can be weighted so that the server can stream medical image data to respective viewports/dedicated buffers as a function of priority. The AI component 414 can facilitate determining or inferring medical image data viewing/rendering needs and facilitate weighting requests for respective chunks of medical image data. Thus, each buffer can request images with a certain weightage. In the case of medical images, one of the viewports may be active. For example, if a user is scrolling only in viewport 1 (or image container 1), the associated dedicated buffer for viewport 1 will request images with a higher weightage than requests associated with other viewports that are not active or less active than viewport 1. The server will prioritize such requests and stream a higher amount of tokens (or frames) based on the weighting. In another words, based on weighting of requests, the higher weighting given a request, the higher priority the server will treat such request. Accordingly, viewports or containers that have higher data needs, e.g., are more active, will be associated with requests having higher weight relative to requests from viewports or containers that have less needs or priority.

It is to be appreciated that an AI component can perform a utility-based analysis with such weighting requests that factors the benefit of making a correct weight versus the costs of an incorrect weighting. In an embodiment, the AI component can make inferences as to priority of a user tasks or needs with respective to an activity in a given viewport. For example, if a high-resolution set of images is required for a given task, e.g., a radiology scan for a tumor, the AI component can up-weight the viewport as a function of the task (or image requirements) in addition to user activity.

In an embodiment, the weighting can also be a function time. If a particular action on a viewport is near completion, the request can be up-weighted so that a final set of data can be streamed and buffered to fulfill last requests associated with a given task.

In the figure, tokens=frames, and data buffer 1 has requested 8 tokens with a weightage of 4. The server will subdivide into sub-collection of weightage. So here 8 tokens come from data buffer 1 with weightage 4. This means there are two sub-collections, which means sub-collection 1 and sub-collection 2 will be served before any other data buffers request. This is how the server will handle the requests coming from different data buffers. Thus, each viewport can have different importance. For example active viewports can be deemed more important than inactive viewports. In another example, one viewport can include the primary study. A download policy can direct the server how to allocate resources to different viewports, which can be context based (active, primary). Accordingly, the download policy can set resource priorities or weightings per viewport. Similarly, in an embodiment, the system 100 can choose to skip frames in some viewports but keep other viewport frame by frame. This can be dictated by a consumer policy and the server responds to these requests.

Figure 6:
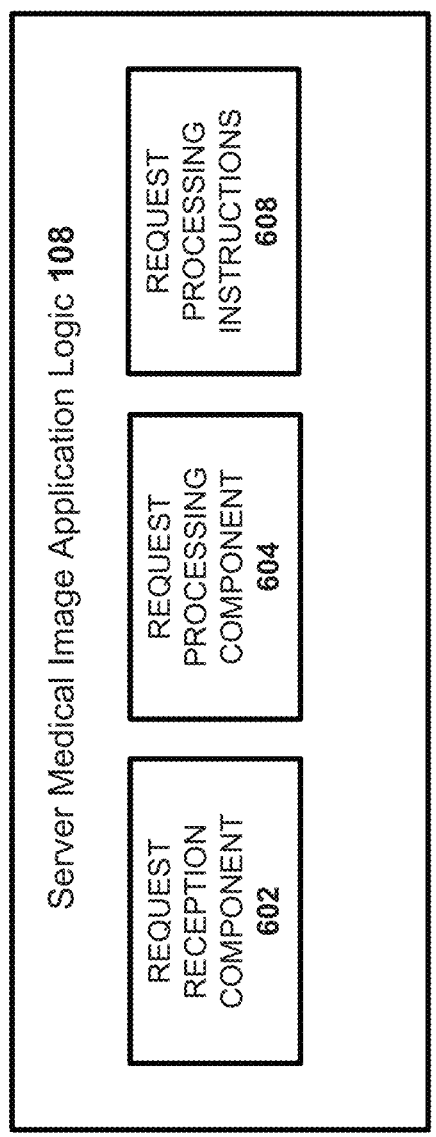
FIG. 6 illustrates example server medical image application logic components in accordance with one or more embodiments of the disclosed subject matter.

FIG. 6 schematically illustrates an embodiment relating to the server medical image application logic 108. As noted a visualization application that renders medical images at client device 118 leverages application logic 108 at the server 102 and application logic 128 at the client device 118. The server logic 108 includes request reception component 602 that receives requests 138 for medical image data from the client device 118. Oftentimes, multiple requests are made as a function of multiple viewports for example. A request processing component 604 processes the incoming requests 138 and prioritizes services the requests as a function of request processing instructions 608 as a function of weightings associated with the respective requests as discussed in detail supra in connection with FIG. 5. The server logic 108 can utilize the artificial intelligence (AI) component and/or associated models to facilitate servicing of the requests.

Given that the visualization application is a distributed application that resides at both server and client, it is to be appreciated that one or more functions performed at the server can in various embodiments be implemented at the client side and vice versa.

Conventional medical image rendering systems are often ineffective at rapidly rendering high-quality medical images due to voluminous size of medical images and limited hardware and network resources. Embodiments described and claimed herein overcome many deficiencies associated with conventional systems through dynamic weighting of data requests, strategic buffering of data across respective dedicated viewport buffers, factoring monitored user activity, learning historical user and task use scenarios, leveraging artificial intelligence and trained model(s) (explicitly and implicitly) to provide for a highly dynamic visualization system 100 that optimizes requesting, streaming, buffering and rendering of medical image data in a dynamic and adaptive manner to facilitate provisioning of a highly efficient visualization work environment, given available hardware and network resources, for a medical professional or the like.

Figure 7:
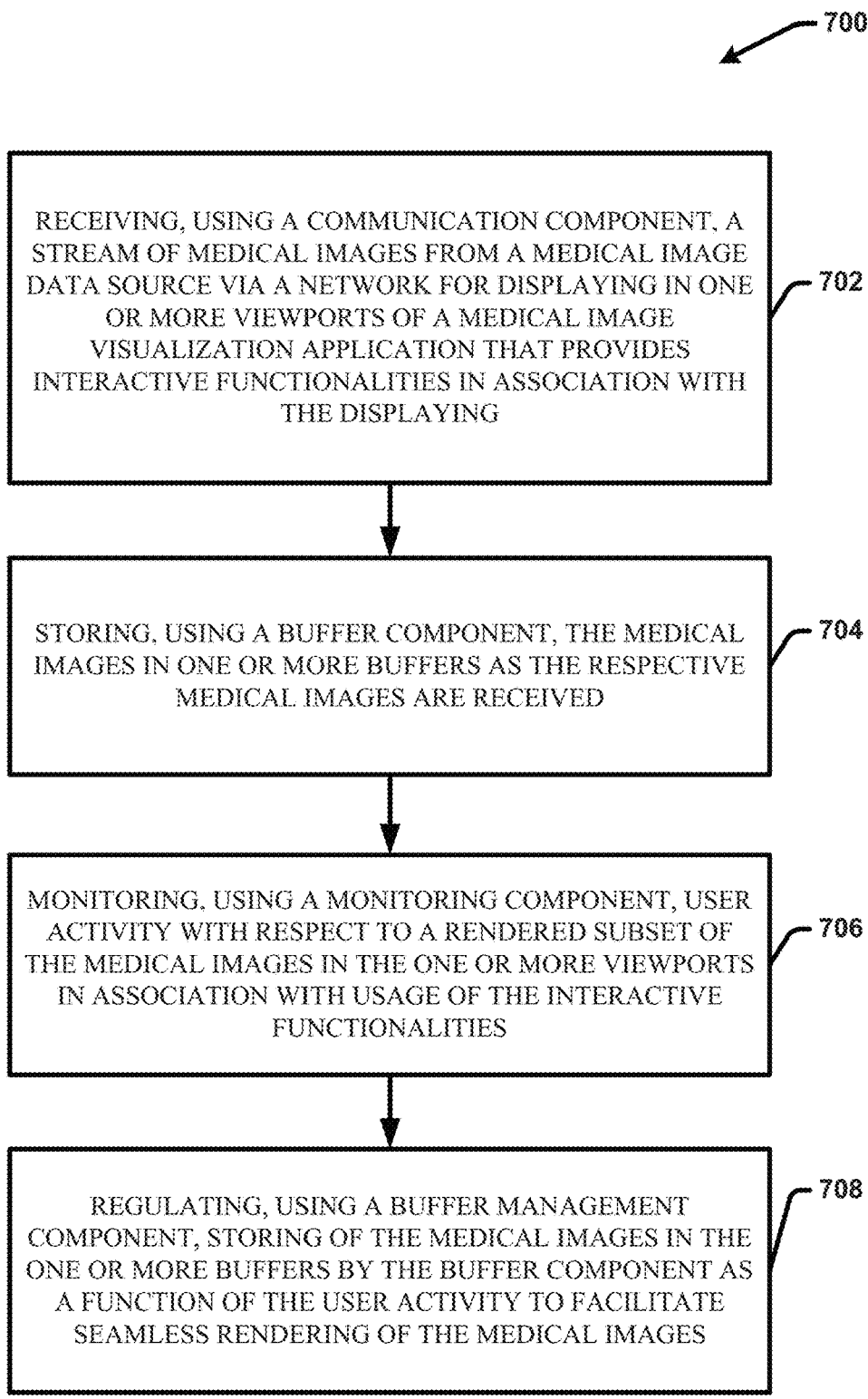
FIG. 7 illustrates a high-level flow diagram of an example process that facilitates seamless rendering of medical images via a web-based medical imaging viewer in accordance with one or more embodiments of the disclosed subject matter.

FIG. 7 schematically illustrates a flow diagram of a methodology 700 in accordance with one or more embodiments. It is to be appreciated that respective acts can be carried out without requiring all or other acts. At 702 a stream of medical images is received (e.g., using a communications component 120) from a medical image data source via a network for displaying in one or more viewports of a medical image visualization application that provides interactive functionalities in association with the displaying. In other words, a user (e.g., medical worker) is employing the methodology 700 in connection with viewing medical image data in a visualization application. As discussed, a server streams such medical image data to a client device employed by the user, and the medical image data is rendered via the visualization application. The visualization application can utilize one or more viewports. A viewport can be akin to a viewing window, portal, display or the like. Oftentimes, medical workers multi-task or multi-view by viewing multiple images across one or more displays.

At 704, the streamed medical images from the server are stored in one or more buffers as the respective medical images (or medical image data) are received. The received medical image data is respectively buffered to facilitate seamless rendering of respective medical images. For example, if network bandwidth is insufficient, the streamed medical image data can result in choppy rendering. By buffering such medical image data, rendering of the medical image data can be presented in a seamless and smooth manner. However, medical image data can often be voluminous, and network and hardware resources limited. Consequently, conventional medical image rendering systems often fall short due to inefficient resource allocation and data management. The subject innovation facilitates real-time assessment of data needs at a viewport and user activity and inferred future activity level to optimize resource allocation (e.g., buffering, streaming priority, weighting, etc.) to facilitate seamless rendering of medical image data as needed based on limited resources.

At 706, user activity is monitored (e.g., using a monitoring component 410) with respect to a rendered subset of the medical images in the one or more viewports in association with usage of the interactive functionalities. By monitoring user activity, data needs with respect to streaming, prioritizing streaming, data requests, buffering, etc., can be determined or inferred in order to facilitate provisioning and rendering of medical image data per determined or inferred user needs. In an embodiment, the AI component can facilitate making such determinations or inferences using models (trained explicitly or implicitly) that leverage historical usage cases, user preferences, known tasks, data types, etc. Accordingly, based on context of a user, task(s), resources, etc. data requests, data buffering, data rendering, can be regulated to optimize a visualization experience given a set of resources and associated constraints or limitations.

At 708, regulation (e.g., using a buffer management component) of storing of the medical images in the one or more buffers by the buffer component is performed as a function of the user activity to facilitate seamless rendering of the medical images.

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 8, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 8:
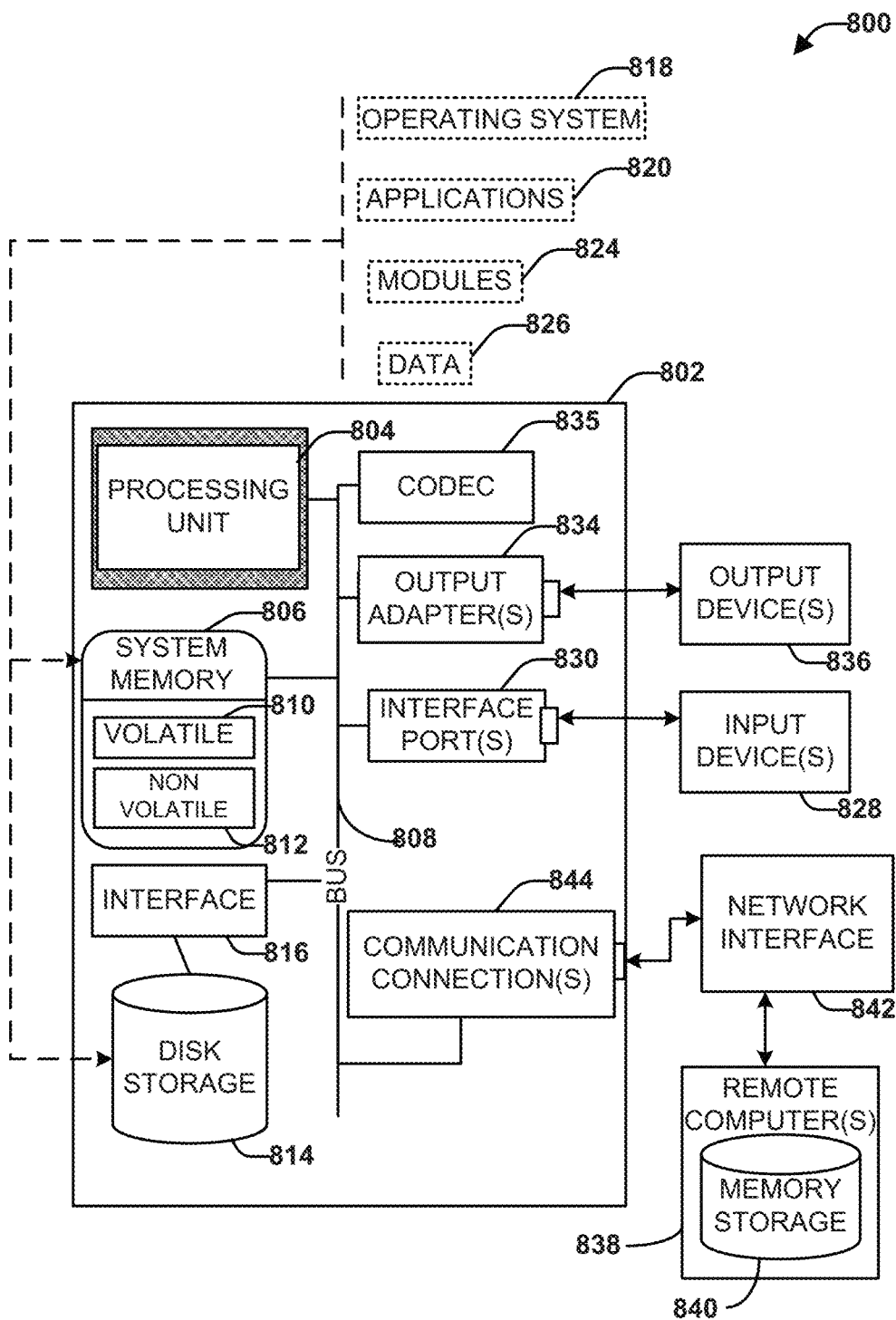
FIG. 8 illustrates a block diagram of an example, non-limiting operating environment in which one or more embodiments described herein can be facilitated.

With reference to FIG. 8, an example environment 800 for implementing various aspects of the claimed subject matter includes a computer 802. The computer 802 includes a processing unit 804, a system memory 806, a codec 835, and a system bus 808. The system bus 808 couples system components including, but not limited to, the system memory 806 to the processing unit 804. The processing unit 804 can be any of various available processors. Dual microprocessors and other multiprocessor architectures also can be employed as the processing unit 804.

The system bus 808 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13104), and Small Computer Systems Interface (SCSI).

The system memory 806 includes volatile memory 810 and non-volatile memory 812, which can employ one or more of the disclosed memory architectures, in various embodiments. The basic input/output system (BIOS), containing the basic routines to transfer information between elements within the computer 802, such as during start-up, is stored in non-volatile memory 812. In addition, according to present innovations, codec 835 can include at least one of an encoder or decoder, wherein the at least one of an encoder or decoder can consist of hardware, software, or a combination of hardware and software. Although, codec 835 is depicted as a separate component, codec 835 can be contained within non-volatile memory 812. By way of illustration, and not limitation, non-volatile memory 812 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 812 can employ one or more of the disclosed memory devices, in at least some embodiments. Moreover, non-volatile memory 812 can be computer memory (e.g., physically integrated with computer 802 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 810 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 802 can also include removable/non-removable, volatile/non-volatile computer storage medium. FIG. 8 illustrates, for example, disk storage 814. Disk storage 814 includes, but is not limited to, devices like a magnetic disk drive, solid state disk (SSD), flash memory card, or memory stick. In addition, disk storage 814 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 814 to the system bus 808, a removable or non-removable interface is typically used, such as interface 816. It is appreciated that disk storage 814 can store information related to an entity. Such information might be stored at or provided to a server or to an application running on an entity device. In one embodiment, the entity can be notified (e.g., by way of output device(s) 836) of the types of information that are stored to disk storage 814 or transmitted to the server or application. The entity can be provided the opportunity to opt-in or opt-out of having such information collected or shared with the server or application (e.g., by way of input from input device(s) 828).

It is to be appreciated that FIG. 8 describes software that acts as an intermediary between entities and the basic computer resources described in the suitable operating environment 800. Such software includes an operating system 818. Operating system 818, which can be stored on disk storage 814, acts to control and allocate resources of the computer system 802. Applications 820 take advantage of the management of resources by operating system 818 through program modules 824, and program data 826, such as the boot/shutdown transaction table and the like, stored either in system memory 806 or on disk storage 814. It is to be appreciated that the claimed subject matter can be implemented with various operating systems or combinations of operating systems.

An entity enters commands or information into the computer 802 through input device(s) 828. Input devices 828 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 804 through the system bus 808 via interface port(s) 830. Interface port(s) 830 include, for example, a serial port, a parallel port, a game port, and a universal serial bus (USB). Output device(s) 836 use some of the same type of ports as input device(s) 828. Thus, for example, a USB port can be used to provide input to computer 802 and to output information from computer 802 to an output device 836. Output adapter 834 is provided to illustrate that there are some output devices 836 like monitors, speakers, and printers, among other output devices 836, which require special adapters. The output adapters 834 include, by way of illustration and not limitation, video and sound cards that provide a means of connection between the output device 836 and the system bus 808. It should be noted that other devices or systems of devices provide both input and output capabilities such as remote computer(s) 838.

Computer 802 can operate in a networked environment using logical connections to one or more remote computers, such as remote computer(s) 838. The remote computer(s) 838 can be a personal computer, a server, a router, a network PC, a workstation, a microprocessor based appliance, a peer device, a smart phone, a tablet, or other network node, and typically includes many of the elements described relative to computer 802. For purposes of brevity, only a memory storage device 840 is illustrated with remote computer(s) 838. Remote computer(s) 838 is logically connected to computer 802 through a network interface 842 and then connected via communication connection(s) 844. Network interface 842 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereof, packet switching networks, and Digital Subscriber Lines (DSL).

Communication connection(s) 844 refers to the hardware/software employed to connect the network interface 842 to the bus 808. While communication connection 844 is shown for illustrative clarity inside computer 802, it can also be external to computer 802. The hardware/software necessary for connection to the network interface 842 includes, for exemplary purposes only, internal and external technologies such as, modems including regular telephone grade modems, cable modems and DSL modems, ISDN adapters, and wired and wireless Ethernet cards, hubs, and routers.

The illustrated aspects of the disclosure may also be practiced in distributed computing environments where certain tasks are performed by remote processing devices that are linked through a communications network. In a distributed computing environment, program modules can be located in both local and remote memory storage devices.

Figure 9:
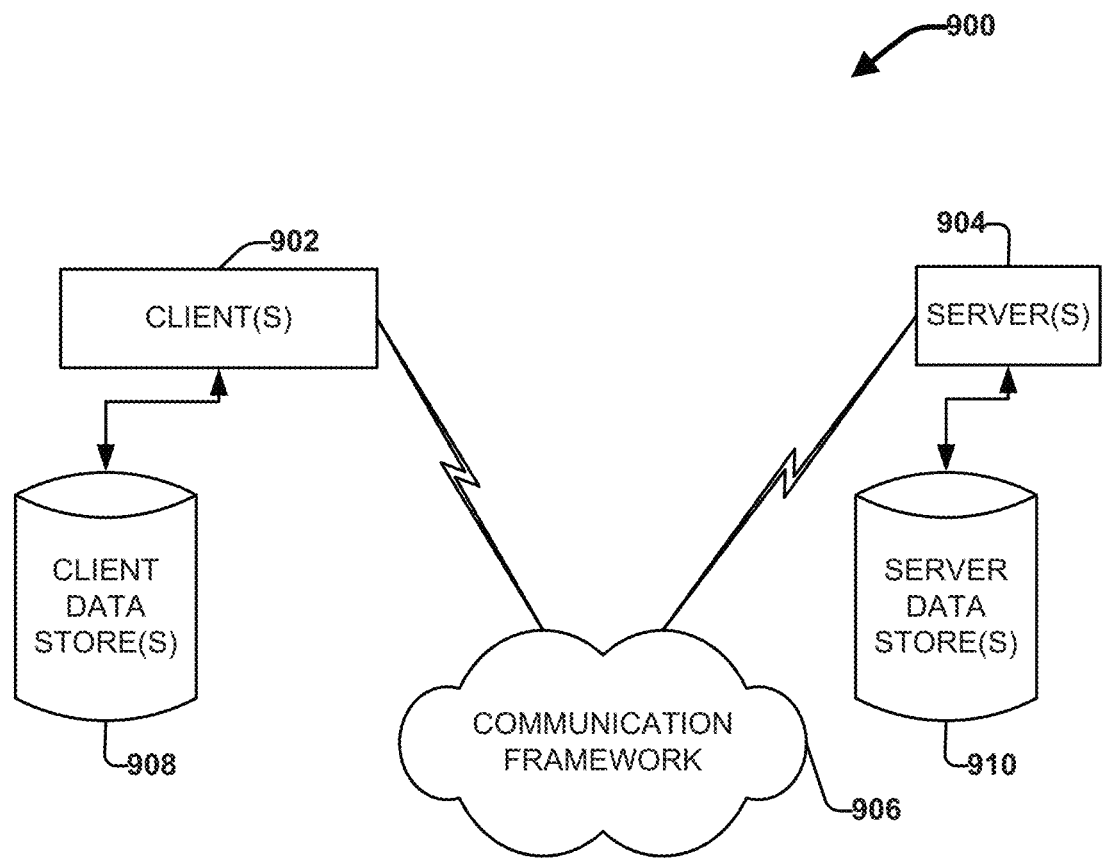
FIG. 9 illustrates a block diagram of another example, non-limiting operating environment in which one or more embodiments described herein can be facilitated.

Referring to FIG. 9, there is illustrated a schematic block diagram of a computing environment 900 in accordance with this disclosure in which the subject systems (e.g., system 100 and the like), methods and computer readable media can be deployed. The computing environment 900 includes one or more client(s) 902 (e.g., laptops, smart phones, PDAs, media players, computers, portable electronic devices, tablets, and the like). The client(s) 902 can be hardware and/or software (e.g., threads, processes, computing devices). The computing environment 900 also includes one or more server(s) 904. The server(s) 904 can also be hardware or hardware in combination with software (e.g., threads, processes, computing devices). The servers 904 can house threads to perform transformations by employing aspects of this disclosure, for example. In various embodiments, one or more components, devices, systems, or subsystems of system 100 can be deployed as hardware and/or software at a client 902 and/or as hardware and/or software deployed at a server 904. One possible communication between a client 902 and a server 904 can be in the form of a data packet transmitted between two or more computer processes wherein the data packet may include healthcare related data, training data, AI models, input data for the AI models, encrypted output data generated by the AI models, and the like. The data packet can include a metadata, e.g., associated contextual information, for example. The computing environment 900 includes a communication framework 906 (e.g., a global communication network such as the Internet, or mobile network(s)) that can be employed to facilitate communications between the client(s) 902 and the server(s) 904.

Communications can be facilitated via a wired (including optical fiber) and/or wireless technology. The client(s) 902 include or are operatively connected to one or more client data store(s) 908 that can be employed to store information local to the client(s) 902 (e.g., associated contextual information). Similarly, the server(s) 904 are operatively include or are operatively connected to one or more server data store(s) 910 that can be employed to store information local to the servers 904.

In one embodiment, a client 902 can transfer an encoded file, in accordance with the disclosed subject matter, to server 904. Server 904 can store the file, decode the file, or transmit the file to another client 902. It is to be appreciated, that a client 902 can also transfer uncompressed file to a server 904 can compress the file in accordance with the disclosed subject matter. Likewise, server 904 can encode video information and transmit the information via communication framework 906 to one or more clients 902.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "subsystem" "platform," "layer," "gateway," "interface," "service," "application," "device," and the like, can refer to and/or can include one or more computer-related entities or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in the memory, wherein the computer executable components comprise:
a communication component that receives a stream of medical images from a medical image data source via a network for displaying in one or more viewports of a medical image visualization application that provides interactive functionalities in association with the displaying;
a buffer component that stores the medical images, in one or more buffers, as the respective medical images are received;
a monitoring component that monitors user activity with respect to a rendered subset of the medical images in the one or more viewports in association with usage of the interactive functionalities;
a buffer management component that regulates storing of the medical images in the one or more buffers by the buffer component as a function of the user activity to facilitate seamless rendering of the medical images; and
an artificial intelligence (AI) component that facilitates regulating a speed of buffering in the one or more buffers as a function of inferred future user activity within respective viewports of the one or more viewports.

2. The system of claim 1, further comprising a rendering component that regulates speed of rendering of a subset of the medical images as a function of amount of the subset of medical images data respectively buffered.

3. The system of claim 1, wherein each of the one or more viewports has a dedicated buffer.

4. The system of claim 3, wherein the speed of buffering in respective dedicated buffers is a function of user activity within the respective viewports.

5. The system of claim 4, wherein the speed of buffering in the respective dedicated buffers is a function of network bandwidth.

6. The system of claim 3, wherein the artificial intelligence (AI) component facilitates regulating the speed of buffering in respective dedicated buffers as a function of the inferred future user activity within the respective viewports.

7. The system of claim 1, wherein the AI component facilitates regulating rendering of respective medical images as a function of the inferred future user activity within the respective viewports.

8. The system of claim 3, further comprising a rendering component that renders a subset of the medical images in the respective viewports, and regulates the rendering of the subset of the medical images as a function of medical image data buffered in the respective dedicated buffers.

9. The system of claim 8, wherein the rendering component skips rendering of frames of the respective medical image data to maintain frame per second rendering of the respective medical image data.

10. The system of claim 9, further comprising a notification component that alerts a viewer when frames of the respective medical image data are skipped.

11. The system of claim 5, further comprising a weighting component that weights requests for the respective medical image data as a function of priority of display criteria per viewport.

12. A computer-implemented method that employs a processor and memory to implement acts, comprising
receiving, using a communication component, a stream of medical images from a medical image data source via a network for displaying in one or more viewports of a medical image visualization application that provides interactive functionalities in association with the displaying;
storing, using a buffer component, the medical images in one or more buffers as the respective medical images are received;
monitoring, using a monitoring component, user activity with respect to a rendered subset of the medical images in the one or more viewports in association with usage of the interactive functionalities; and
regulating, using a buffer management component, storing of the medical images in the one or more buffers by the buffer component as a function of the user activity to facilitate seamless rendering of the medical images, wherein the regulating comprises facilitating regulating, using an artificial intelligence (AI) component, a speed of buffering in the one or more buffers as a function of inferred future user activity within respective viewports of the one or more viewports.

13. The method of claim 12, further comprising regulating, using a rendering component, speed of rendering of a subset of the medical images as a function amount of the subset of medical images data respectively buffered.

14. The method of claim 12, wherein each of the one or more viewports has a dedicated buffer.

15. The method of claim 14, wherein the speed of buffering in respective dedicated buffers is a function of user activity within the respective viewports.

16. The method of claim 15, wherein the speed of buffering in the respective dedicated buffers is a function of network bandwidth.

17. The method of claim 14, wherein the facilitating regulating, using the AI component, comprises regulating the speed of buffering in respective dedicated buffers as a function of inferred future user activity within the respective viewports.

18. The method of claim 12, wherein the AI component facilitates regulating rendering of the respective medical images as a function of the inferred future user activity within the respective viewports.

19. The system of claim 16, further comprising a weighting component that weights requests for the respective medical image data as a function of priority of display criteria per viewport.

20. A non-transitory machine-readable storage medium, comprising executable instructions that, when executed by a processor, facilitate performance of operations, comprising:
receiving a stream of medical images from a medical image data source via a network for displaying in one or more viewports of a medical image visualization application that provides interactive functionalities in association with the displaying;
storing the medical images in one or more buffers as the respective medical images are received;
monitoring user activity with respect to a rendered subset of the medical images in the one or more viewports in association with usage of the interactive functionalities; and
regulating storing of the medical images in the one or more buffers by the buffer component as a function of the user activity to facilitate seamless rendering of the medical images, comprising regulating, using an artificial intelligence (AI) component, a speed of buffering in the one or more buffers as a function of inferred future user activity within respective viewports of the one or more viewports.

* * * * *